(12) United States Patent
Pelletier et al.

(10) Patent No.: US 9,182,518 B2
(45) Date of Patent: Nov. 10, 2015

(54) SENSOR CONDITIONING APPARATUS, SYSTEMS, AND METHODS

(75) Inventors: Michael T. Pelletier, Houston, TX (US); Christopher Michael Jones, Houston, TX (US); Gary D. Althoff, Houston, TX (US); Mark A. Proett, Missouri City, TX (US); Robert Atkinson, Richmond, TX (US); Jim W. Stoddard, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/374,023

(22) PCT Filed: Jan. 31, 2012

(86) PCT No.: PCT/US2012/023374
§ 371 (c)(1),
(2), (4) Date: Jul. 23, 2014

(87) PCT Pub. No.: WO2013/115803
PCT Pub. Date: Aug. 8, 2013

(65) Prior Publication Data
US 2015/0007631 A1    Jan. 8, 2015

(51) Int. Cl.
*G01V 13/00* (2006.01)
*G01N 33/28* (2006.01)
*E21B 49/10* (2006.01)

(52) U.S. Cl.
CPC .............. *G01V 13/00* (2013.01); *E21B 49/10* (2013.01); *G01N 33/2823* (2013.01)

(58) Field of Classification Search
CPC ........... G01V 13/00; G01V 3/00; G01V 8/00; G01N 33/2823; G01N 33/28; G01N 33/2835; E21B 49/08; E21B 48/10

USPC .......................................................... 73/1.02
See application file for complete search history.

(56) References Cited

U.S. PATENT DOCUMENTS 2,152,036 A    3/1939   Froh
3,813,936 A    6/1974   Urbanosky et al.
(Continued)

FOREIGN PATENT DOCUMENTS

WO    WO-2009/052235 A1    4/2009
WO    WO-2013115803 A1     8/2013

OTHER PUBLICATIONS

"Australian Application Serial No. 2012363316, Examination Report No. 1 mailed Sep. 5, 2014", 5 pgs.
(Continued)

*Primary Examiner* — Lisa Caputo
*Assistant Examiner* — Philip Cotey
(74) *Attorney, Agent, or Firm* — Schwegman Lundberg & Woessner, P.A.; Benjamin Fite

(57) ABSTRACT

In some embodiments, an apparatus and a system, as well as a method and an article may operate to move fluid from at least one fluid container into a flow line so as to cause the fluid to contact at least one surface having a condition affecting sensor information provided by a sensor. Additional activities may include adjusting operation of a fluid transport mechanism based on the sensor information and baseline information, to continue moving the fluid and change the condition until the fluid is depleted from the at least one fluid container or the sensor information conforms to the baseline information to a selected degree. Additional apparatus, systems, and methods are disclosed.

21 Claims, 7 Drawing Sheets

(56) References Cited

U.S. PATENT DOCUMENTS

| | | | |
|---|---|---|---|
| 4,994,671 | A | 2/1991 | Safinya et al. |
| 6,161,435 | A | 12/2000 | Bond et al. |
| 6,350,986 | B1 | 2/2002 | Mullins et al. |
| 6,748,328 | B2 | 6/2004 | Storm, Jr. |
| 6,912,904 | B2 | 7/2005 | Storm, Jr. et al. |
| 7,251,565 | B2 | 7/2007 | Storm, Jr. et al. |
| 7,677,307 | B2 | 3/2010 | Vasques et al. |
| 2001/0014477 | A1* | 8/2001 | Pelc et al. ............... 73/863.02 |
| 2001/0020675 | A1* | 9/2001 | Tubel et al. ............ 250/227.11 |
| 2001/0023614 | A1* | 9/2001 | Tubel et al. .............. 73/152.39 |
| 2001/0052427 | A1* | 12/2001 | Eppink et al. .................. 175/40 |
| 2002/0011333 | A1* | 1/2002 | Ward ..................... 166/250.07 |
| 2003/0042021 | A1 | 3/2003 | Bolze et al. |
| 2004/0154380 | A1* | 8/2004 | Walker ........................ 73/49.2 |
| 2006/0288769 | A1* | 12/2006 | Odom ....................... 73/152.22 |
| 2007/0039731 | A1 | 2/2007 | Fox et al. |
| 2008/0093078 | A1* | 4/2008 | Vasques et al. ............... 166/311 |
| 2008/0105567 | A1 | 5/2008 | Okayama et al. |
| 2008/0156077 | A1* | 7/2008 | Flanders ....................... 73/49.6 |
| 2008/0260558 | A1* | 10/2008 | Luongo et al. .................. 73/726 |
| 2009/0120207 | A1* | 5/2009 | Ohtani et al. .............. 73/861.42 |
| 2010/0059669 | A1* | 3/2010 | Jamaluddin et al. ........ 250/269.1 |
| 2010/0132434 | A1* | 6/2010 | Moake .......................... 73/1.82 |
| 2010/0313647 | A1* | 12/2010 | Terabayashi et al. ...... 73/152.55 |
| 2011/0083842 | A1 | 4/2011 | Indo et al. |
| 2012/0018152 | A1 | 1/2012 | Zuilekom et al. |
| 2012/0222852 | A1* | 9/2012 | Pelletier ........................ 166/53 |
| 2013/0099935 | A1* | 4/2013 | Ujereh et al. .............. 340/854.7 |

OTHER PUBLICATIONS

"International Application Serial No. PCT/US2012/023374, International Preliminary Report on Patentability mailed Jan. 3, 2014", 9 pgs.

"International Application Serial No. PCT/US2012/023374, Search Report mailed Jun. 1, 2012", 2 pgs.

"International Application Serial No. PCT/US2012/023374, Written Opinion maild Jun. 1, 2012", 4 pgs.

"Canadian Application Serial No. 2,861.092. Office Action mailed Sep. 23, 2014", 7 pgs.

"Australian Application Serial No. 2012368316, Subsequent Examiners Report mailed Feb. 18, 2015", 5 pgs.

"European Application Serial No. 12867641.8, Supplementary Partial European Search Report mailed Jan. 29, 2015", 7 pgs.

Australian Application Serial No. 2012368316, Response filed Feb. 5 2015 to Examination Report No. 1 mailed Sep. 5, 2014, 17 pgs.

Canadian Application Serial No. 2,861,092, Response filed Mar. 23, 2015 to Office Action mailed Sep. 23, 2014, 29 pgs.

European Application Serial No. 12867641.8, Extended European Search Report mailed May 11, 2015, 12 pgs.

\* cited by examiner

SENSOR CONDITIONING APPARATUS, SYSTEMS, AND METHODS

PRIORITY APPLICATION

This application is a U.S. National Stage Filing under 35 U.S.C. 371 from International Application No. PCT/US2012/023374, filed on 31 Jan. 2012, and published as WO 2013/115803 A1 on 8 Aug. 2013; which application and publication are incorporated herein by reference in their entirety.

BACKGROUND

Understanding the structure and properties of geological formations can reduce the cost of drilling wells for oil and gas exploration. To help determine geological formation characteristics, a variety of formation fluid sensors may be deployed down hole.

Down hole sensors often experience radical changes in environmental conditions, including temperature variations, pressure variations, and vibration. Sensors may also experience what is known by those of ordinary skill in the art as "carryover", or memory effects from previous measurements. For example, in an optical system, material from previous formation fluid analyses may adhere to observation windows, affecting the accuracy of future measurements. Sensors, and the instruments connected to them, may also experience internal drift over time. Any of these variations may contribute to reduced measurement accuracy.

DETAILED DESCRIPTION

Figure 1:
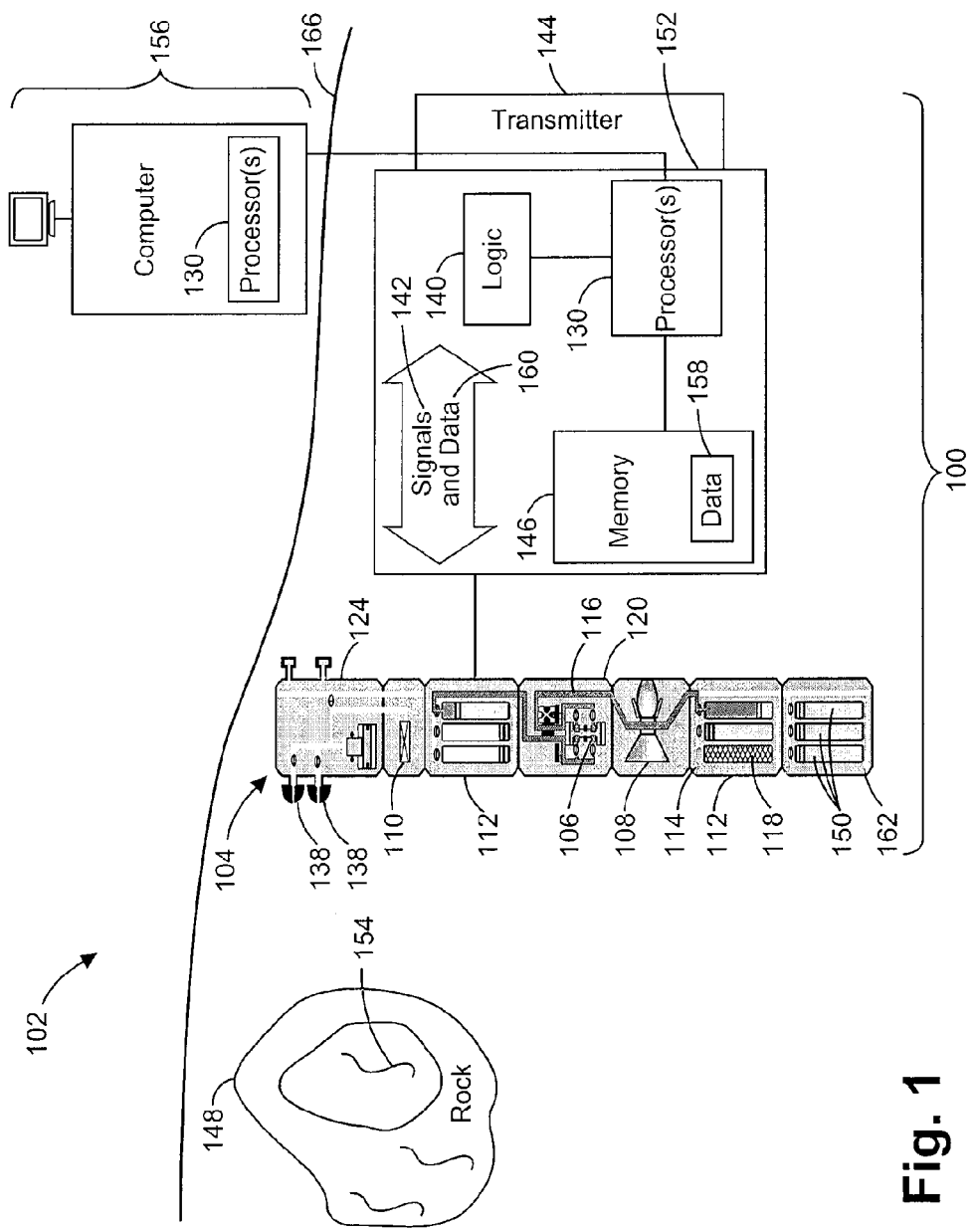
FIG. 1 is a block diagram of an apparatus and system according to various embodiments of the invention.

During the process of drilling a well it may be desirable to sample formation fluid. To do so, the formation fluid can be pumped and filtered to reduce contamination, the major constituent often being drilling fluid filtrate. Sensors provide an estimate of various properties of the fluid mixture during the pumpout. Some of these sensors fall into the optical class.

The optical class of sensors typically employ an energy source (e.g., a light source) for sample illumination, one or more windows for interacting the energy with the sample, optical elements for conditioning the energy, and a detector to detect at least one property of the energy (e.g., intensity). After contamination is reduced to the desired level, the pumpout is determined to be sufficient and an aliquot of the formation fluid is placed in a container, often called a "sample chamber" that can be brought to the surface, and tested for desired properties. Sometimes the windows or other surfaces associated with the sensors (i.e., surfaces having a condition that affects the measurement values rendered by the sensor) are affected by the contamination or other properties of the fluid, so that carryover results, and future measurements are compromised.

Various embodiments of the invention can be used to mitigate the effects of carryover, and perhaps the effects of other down hole environmental variations, by:

1) Providing a standard to normalize the sensor response down hole.
2) Cleaning contamination via solvents.
3) Cleaning contamination via chemical reaction (e.g., oxidation effects).
4) Cleaning via surface adsorption exchange (e.g., cation exchange).
5) Tool passivation after $H_2S$ sampling (e.g., using $Na_2Ca_3$ to neutralize residual $H_2S$).
6) Flocculating loose particles.
7) Sweeping with a viscosity-enhanced fluid.
8) Using designer fluids as calibration standards prior to making additional measurements.

The details of how these activities can be implemented according to various embodiments will now be described.

To begin, a set of fluids may be formulated to carry out the various activities noted above. Such fluids are designated as "designer fluids" herein. The set of designer fluids taken down hole will thus be determined by the activities desired.

Between formation measurements, and before new station sampling occurs, one or more of the designer fluids is placed in contact with the sensors of the tool. The fluids are selected according the sensor type and the contamination type expected.

The sensor is now operated to obtain measurements for tuning. The fluid in contact with the sensor can be pressurized for concentration changes, if desired. The fluid can be reacted with another fluid or formation fluid to effect composition changes. The fluid can be mixed with another fluid or formation fluid to effect composition changes as well.

At this point, the sensor response can be normalized for the current environment and/or instrument drift. This includes changes brought about by changes in the baseline measurement, sensitivity, resolution, and nonlinear effects. Sensor measurements continue while pumpout is performed, until the measurements conform to an appropriate baseline value (that is normally preselected and stored in a memory, to be accessed for comparison with actual measurements during the normalization process).

When the supply of fluid is depleted, or when conformance is achieved, actual fluid sampling with the sensor can resume. Sampling may even occur using the same sample chambers that formerly contained the designer fluid, if they are properly flushed or diluted.

This process is repeated for each down hole sensor, as desired. It should be noted that while the various embodiments described herein are directed to an optical sensor for reasons of clarity and simplicity, any type of sensor that contacts a fluid (or is associated with a surface having a condition that affects sensor measurement values, the condition being affected by contact with the fluid in turn) may benefit from the mechanism described herein.

In some embodiments, a down hole charged reservoir is used to deliver a designer fluid into the tool housing to contact a sensor, or surface associated with the sensor, between pumpout stations (e.g., selected geographic locations along the well bore). A nitrogen-backed sampling cylinder, for example, could be used with a designer fluid in such a reservoir.

One or more chambers can be used to dispense one or more corresponding designer fluids, perhaps using a pump. Some or all of the chamber contents may be dispensed using the pump operating in the forward direction, or in reverse, as a metering activity. The pump may also be used to reciprocate the fluid to ensure good fluid mixing and efficient sensor contact. The pump may be used in conjunction with valve settings to increase or decrease the pressure of the fluid (i.e., pressurize the fluid).

The fluid can be designed with an optical signature (or other sensor-specific signature) for normalization. Pressure (induced by the pump) may be used to change the concentration (e.g., density) of the fluid, which can be more effective if the fluid has been chosen to have a high compressibility.

Sensor measurements may suggest when the sensor has been sufficiently reconditioned. For example, when the acquired data is within a specified numerical distance of the baseline, the sensor may be considered ready for further measurement.

In some embodiments, the sample chamber is designed as a flow through chamber, with an inlet port and an outlet port, to allow purging of dead volumes (e.g., air pockets) or calibration fluid. A second outlet port may act as an inspection port for a plug-in sensor (e.g., a density, resistivity, or optical sensor) to monitor some characteristic of the fluid, as a quality control mechanism.

Formation fluid may also be pushed into and emptied out of the chamber to dilute/flush away dead volume. In some embodiments, multiple chambers may be used to mix multiple standards.

Designer fluids may include ultraviolet, visible, near infrared and medium infra-red active compounds, such as salts (e.g., ammonia or ammonium chloride), organic acid emulsifying agents (e.g., Citranox™ detergent), aromatic infrared dyes, and oxidizing agents, including photoactive oxidizers and other types of photoactive chemistry. Thus, many embodiments may be realized.

For example, FIG. 1 is a block diagram of an apparatus 100 and system 102 according to various embodiments of the invention. The apparatus 100 may comprise a downhole tool 104 (e.g., a pumped formation evaluation tool or a reservoir description tool) that includes one or more sensors 108 (e.g., an optical fluid identification (OFID) subsystem, a pressure gauge, a pressure transducer, a strain gauge, etc.). The apparatus 100 might also include quartz gauge subsystem (QGS) 110.

One or more multi-chamber subsystems (MCS) 112, also known as a "multi-chamber sampler" or "sampling sub" may be included in the apparatus 100. The samplers 112 provide individual selection of fluid storage modules 150 coupled to a fluid transport mechanism 106 (e.g., a pump) and valves 114. In this way, designer fluids and fluid samples can be driven to individual module 150, or extracted from individual modules 150, depending on the direction of fluid flow directed by the activity of the fluid transport mechanism 106, and the valves 114.

Some of the modules 150 may include a filter screen assembly 118. A fluid exit 162 may be used to eject fluid from the apparatus 100.

The apparatus 100 may further comprise one or more borehole seals 138 as part of a dual probe subsystem (DPS) 124 to touch the formation 148 and assist in the process of extracting fluid 154 from the formation 148. Thus, the apparatus 100 also comprises one or more fluid transport mechanisms 106 and one or more fluid paths 116 that form part of the flow line.

The sensors 108, and/or surfaces associated with the sensors 108, may be located in the fluid paths 116 so that both formation fluid 154 and designer fluids (housed in modules 150) can be pumped through the tool 104, so as to be in contact with the sensor 108, or in contact with a surface associated with a sensor 108 (e.g., a surface with a temperature measured by a temperature measurement sensor, where the sensor does not directly contact the surface with a characteristic of the fluid, in this case temperature, being measured). It should be noted that, while the downhole tool 104 is shown as such, some embodiments of the invention may be implemented using a wireline logging tool body. However, for reasons of clarity and economy, and so as not to obscure the various embodiments illustrated, this implementation has not been explicitly shown in this figure.

The apparatus 100 may also include logic 140, perhaps comprising a sampling control system. The logic 140 can be used to acquire sensor measurement data 158, including formation fluid property data, and designer fluid property data.

The apparatus 100 may include a data acquisition system 152 to couple to the tool 104, and to receive signals 142 and data 160 generated by the sensor 108, as well as from sensors that may be included in the seals 138. The data acquisition system 152, and/or any of its components, may be located downhole, perhaps in the tool housing or tool body, or at the surface 166, perhaps as part of a computer workstation 156 in a surface logging facility.

In some embodiments of the invention, the apparatus 100 operating down hole can perform the functions of the workstation 156, and these results can be transmitted to the surface 166 and/or used to directly control the downhole sampling system.

The sensor 108 may comprise one or more individual sensors, including a multi-phase flow detector that comprises a densitometer, a bubble point sensor, a compressibility sensor, a speed of sound sensor, an ultrasonic transducer, a viscosity sensor, and/or an optical density sensor.

A control algorithm can be used to program the processor 130 to determine whether the measurement data 160 taken from the sensor 108 conforms to a baseline measurement or measurements. The baseline data may be included as part of stored data 158, which may be stored down hole, or at the surface 166. The fluid transport mechanism 106 may comprise a unidirectional pump or a bidirectional pump in some embodiments. A telemetry transmitter 144 may be used to transmit the data 160 and/or the stored data 158 to the processor(s) 130 at the surface 166.

The tool 104 may be operated in a pump-down configuration to cycle designer fluids past a surface on the sensor 108, or a surface associated with the sensor 108. The flowline that includes the fluid path 116 can be pressurized to increase the pressure, or draw down the pressure below that of the fluid pumping subsystem (FPS) 120, if desired. A chamber valve and filter screen assembly 118, perhaps housed in an MCS 112 forming part of a filtration subsystem, can be used to equalize pressure across valves 114 in the FPS 120 by drawing down the flowline pressure below the FPS 120 pressure using the FPS 120 in a pump-up mode. The filter screen assembly 118 can also be used as an inlet to flush the flowline with filtered borehole fluids 154.

Figure 2:
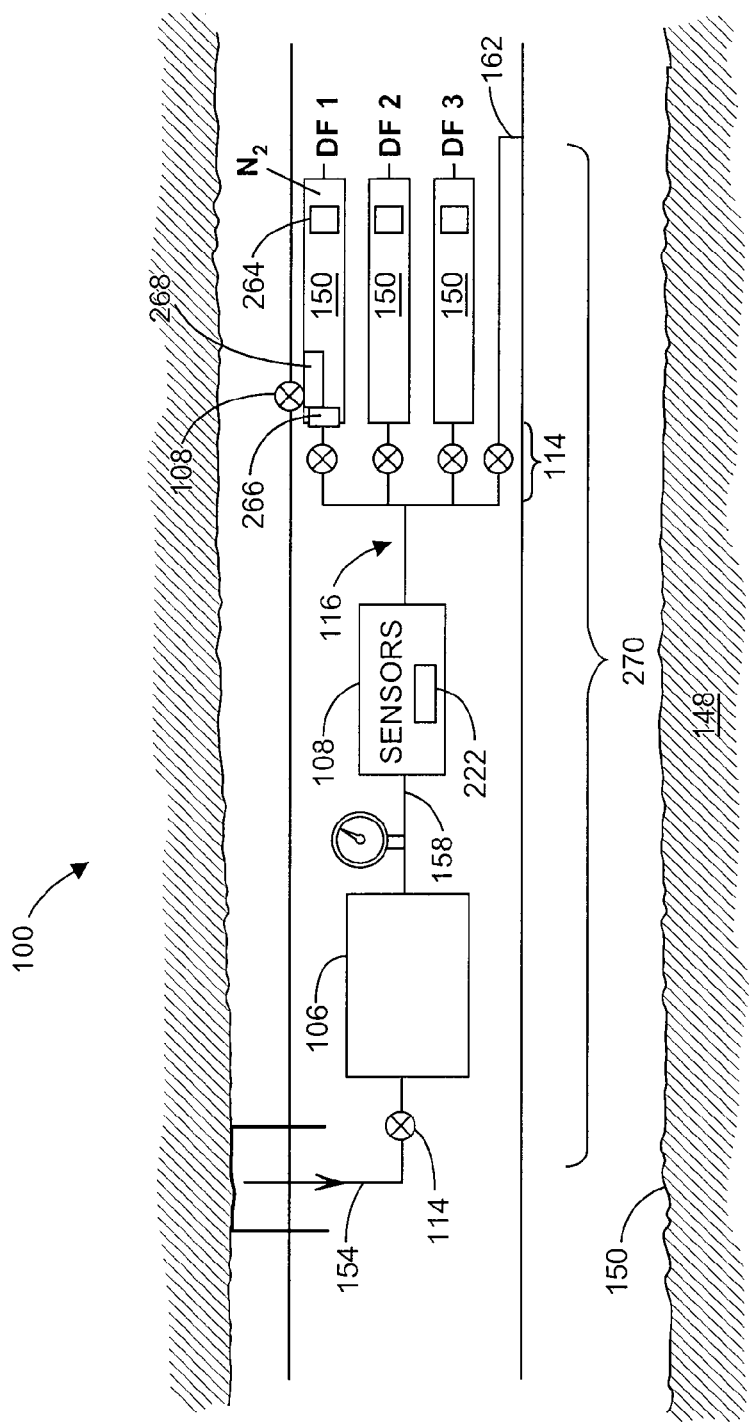
FIG. 2 is a block diagram of an apparatus according to various embodiments of the invention.

FIG. 2 is a block diagram of an apparatus 100 according to various embodiments of the invention. Here the formation fluid 154 is drawn into the flowline 270 (that includes the fluid path 116) from the formation 148, past the sensors 108 (or a surface 222 having a condition monitored by the sensors 108) by the action of the fluid transport mechanism 106. Designer fluids housed in modules 150 can also be moved past the sensors 108 (or surfaces 222 having a condition monitored by the sensors 108) by setting appropriate valves 114 to open or closed states, and using the fluid transport mechanism 106 and/or the movement of a piston 264, perhaps driven by compressed nitrogen.

It should be noted that the term "pumping" as used herein means the activity of the fluid transport mechanism 106 and/or the pistons 264 in moving formation fluid and/or designer fluids within the apparatus 100, usually along the fluid path 116. Formation fluid 154 and/or designer fluids may be ejected into the borehole 150 using the fluid exit 162, the fluid transport mechanism 106, and the valves 114.

Figure 3:
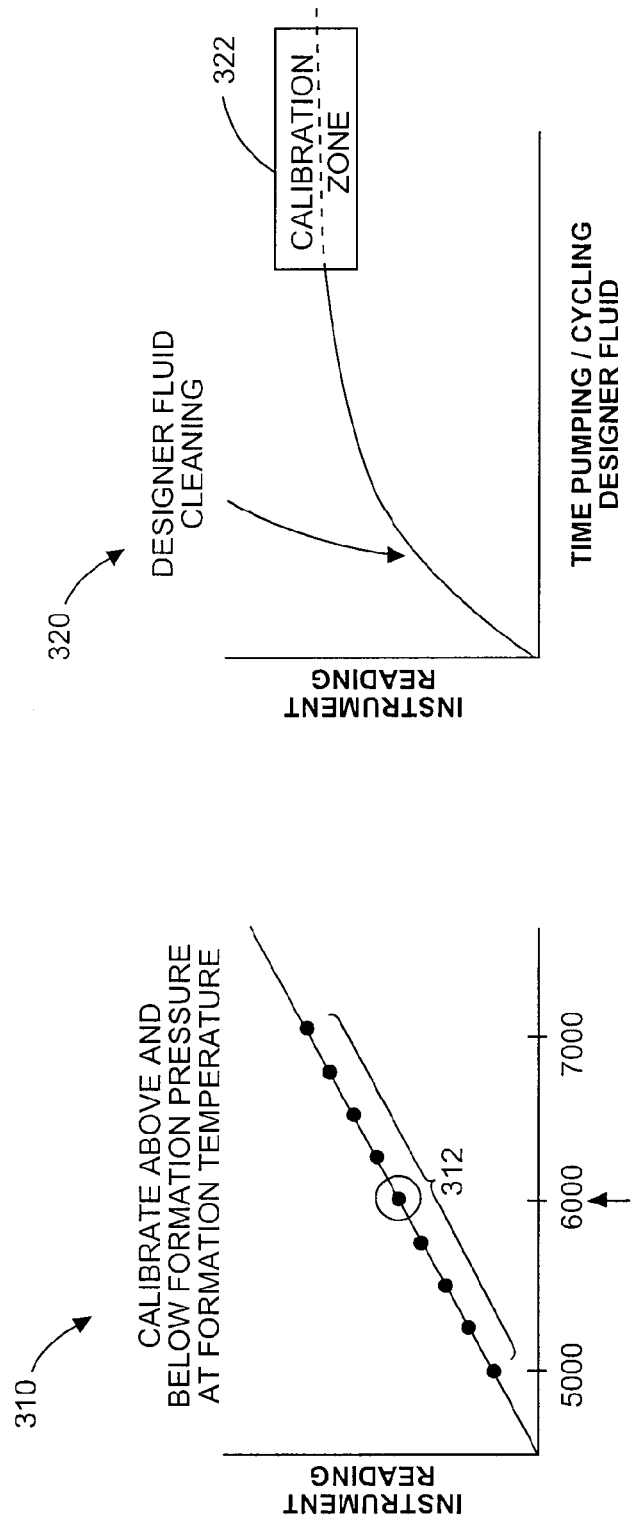
FIG. 3 includes graphs illustrating calibration operations according to various embodiments of the invention.

FIG. 3 includes graphs 310, 320 illustrating calibration operations according to various embodiments of the invention. In graph 310, which might comprise the graph of performance for a formation pressure sensor, several pressure calibration points 312 are shown. Here, a fluid transport mechanism is used to move designer fluid from a fluid container into a flow line, to cause the fluid to contact a measurement surface associated with the sensor. A processor can be used to obtain the resulting sensor reading, and to adjust operation of the fluid transport mechanism based on the sensor information (e.g., the instrument reading) and baseline information. The fluid transport mechanism can be used to move the designer fluid past the measurement surface to change the condition of the measurement surface, until the designer fluid is depleted, or the sensor information conforms to the baseline information to some selected degree (e.g., within ±5%, or ±2%, or ±1%, etc.) over the range of pressure calibration points 312.

Graph 320 illustrates a graph of the time spent moving the designer fluid over the measurement surface versus the sensor reading. Here, the fluid is moved past the measurement surface until the time at which no more fluid is available, or the sensor information conforms to the baseline information to some selected degree (e.g., within ±5%, or ±2%, or ±1%, etc.). In this case, conformance is determined when the instrument reading falls into the calibration zone 322. Thus, referring now to FIGS. 1-3, it can be seen that many embodiments may be realized. For example, an apparatus 100 may comprise one or more fluid containers 150, sensors 108, surfaces that affect the output of the sensors (e.g., surface deposits on the sensing surface of a densitometer may bias the density reading for the densitometer sensor, deposits and buildups in the sensing boundary layer may affect the output of vibrating viscosity sensors, insulating deposits and films may block fluid access to the sensing surface or insulate the electrodes on resistivity sensors, mineral deposits may block optical sensor energy input surface, and organic film buildups (asphaltenes and waxes) on the energy input surface may bias the output of optical sensors), one or more fluid transport mechanisms 106, and one or more processors 130 to control operations.

Thus, in some embodiments, an apparatus 100 comprises at least one fluid container 150 coupled to a flow line 270, a sensor 108, at least one surface having a condition affecting sensor information provided by the sensor (e.g., the surface 222 comprising an optically transparent window in a multi-variate optical element), a fluid transport mechanism 106 to move fluid from the fluid container(s) 150 into the flow line 270, to cause the fluid to contact the surface(s), and a processor 130 to adjust operation of the fluid transport mechanism 106 based on the sensor information and baseline information. The processor 130 may comprise a timer.

The fluid transport mechanism 106 will continue to move the fluid to change the condition, until the down hole supply of fluid is depleted, or the sensor information conforms to the baseline information to a selected degree (e.g., conformance may be achieved when the sensor provides an output reading that is within ±5% of the expected baseline reading for the fluid that is being moved past the surface associated with the sensor).

The sensor may constitute any one of a variety of sensors. For example, among others, the sensor 108 may comprise an optical sensor, a densitometer, or a resistivity sensor.

In some embodiments, fluid transport is regulated by time. That is, transport past the surface is allowed to continue only for a selected time period, even if conformance is not reached by the end of the time period—to conserve the supply of a designer fluid in a container 150.

The surface 222 may form part of the sensor itself, or it may be associated with the sensor in some other way that influences the sensor output. For example, the surface 222 may comprise a surface on the sensor, or an optical window to direct radiated energy to the sensor.

The fluid can be moved in both directions across the surface 222, for more effective cleaning or verification of readings. Thus, in some embodiments, the fluid transport mechanism 106 is reversible, to selectably move the fluid in a first direction across the surface 222, and in a second direction across the surface 222 that is opposite to the first direction.

Multiple containers can be used, as well as multiple fluids, which can be mixed together or reacted to provide a designer fluid. Thus, in some embodiments the apparatus 100 may comprise multiple fluid containers 150 and valves 114, to permit mixing multiple fluids with each other under control of the processor 130, wherein the fluid transport mechanism 106 can be configured to move a mixture of selected ones of the multiple fluids to the sensor 108.

The fluid container may have multiple outlet ports, with one used to monitor the condition of the fluid. Thus, the fluid container 150 may comprise a first outlet port 266 coupled to the flow line 270, and a second outlet port 268 coupled to another sensor 108 to provide fluid property information (as measured within the container) to the processor 130.

The fluid transport mechanism may include a number of devices, working alone or in concert, such as pumps, accumulators (e.g., as a source of pressurized gas), and check valves. Thus, the fluid transport mechanism 106 itself may comprise at least one of a pump, an accumulator, or a valve.

The fluid container may include a flow-through container that can be purged as desired, perhaps using formation fluid. Thus, the fluid container 150 may comprise a flow-through fluid container with at least one inlet and at least one outlet. Still further embodiments may be realized.

Figure 4:
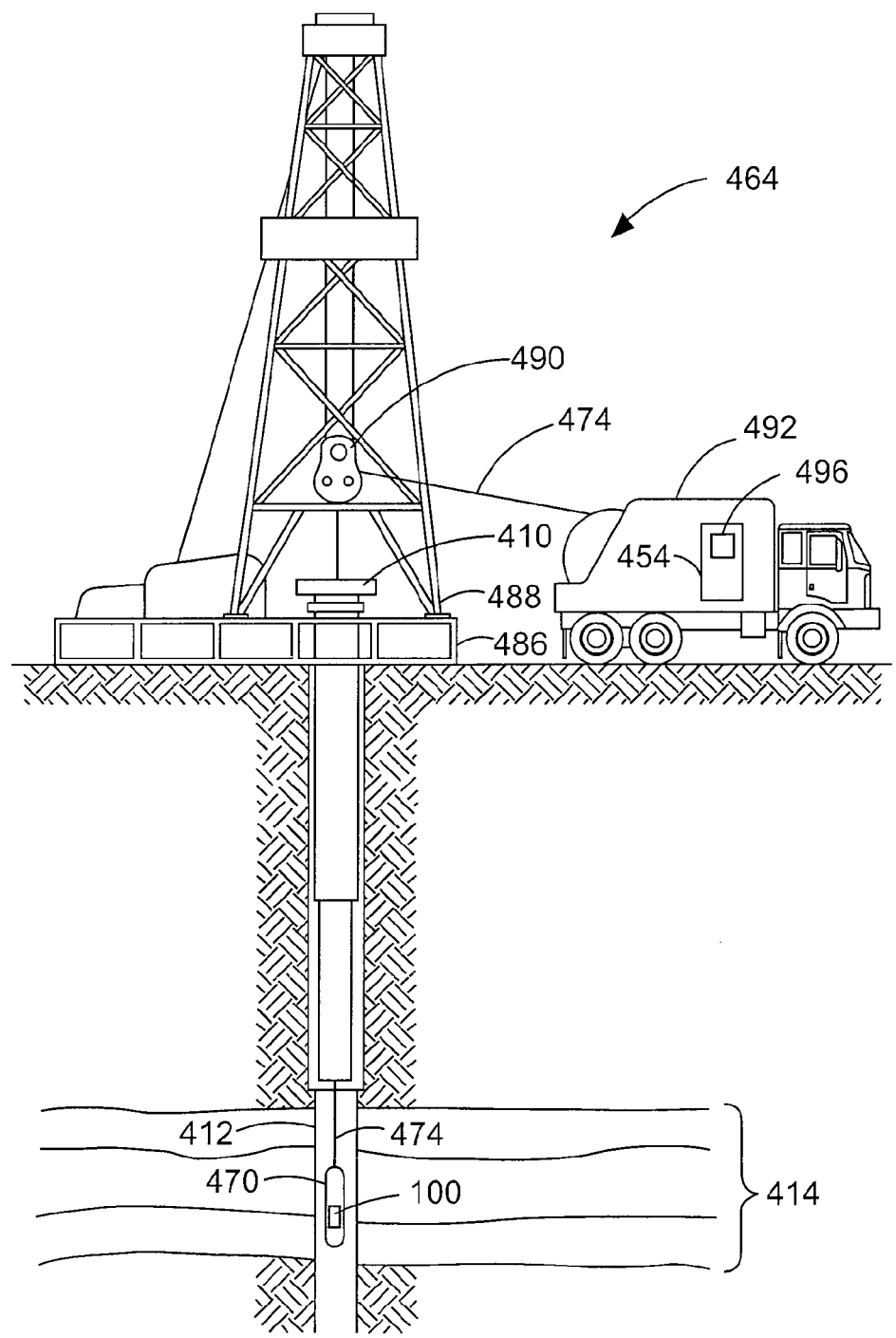
FIG. 4 illustrates a wireline system embodiment of the invention.
Figure 5:
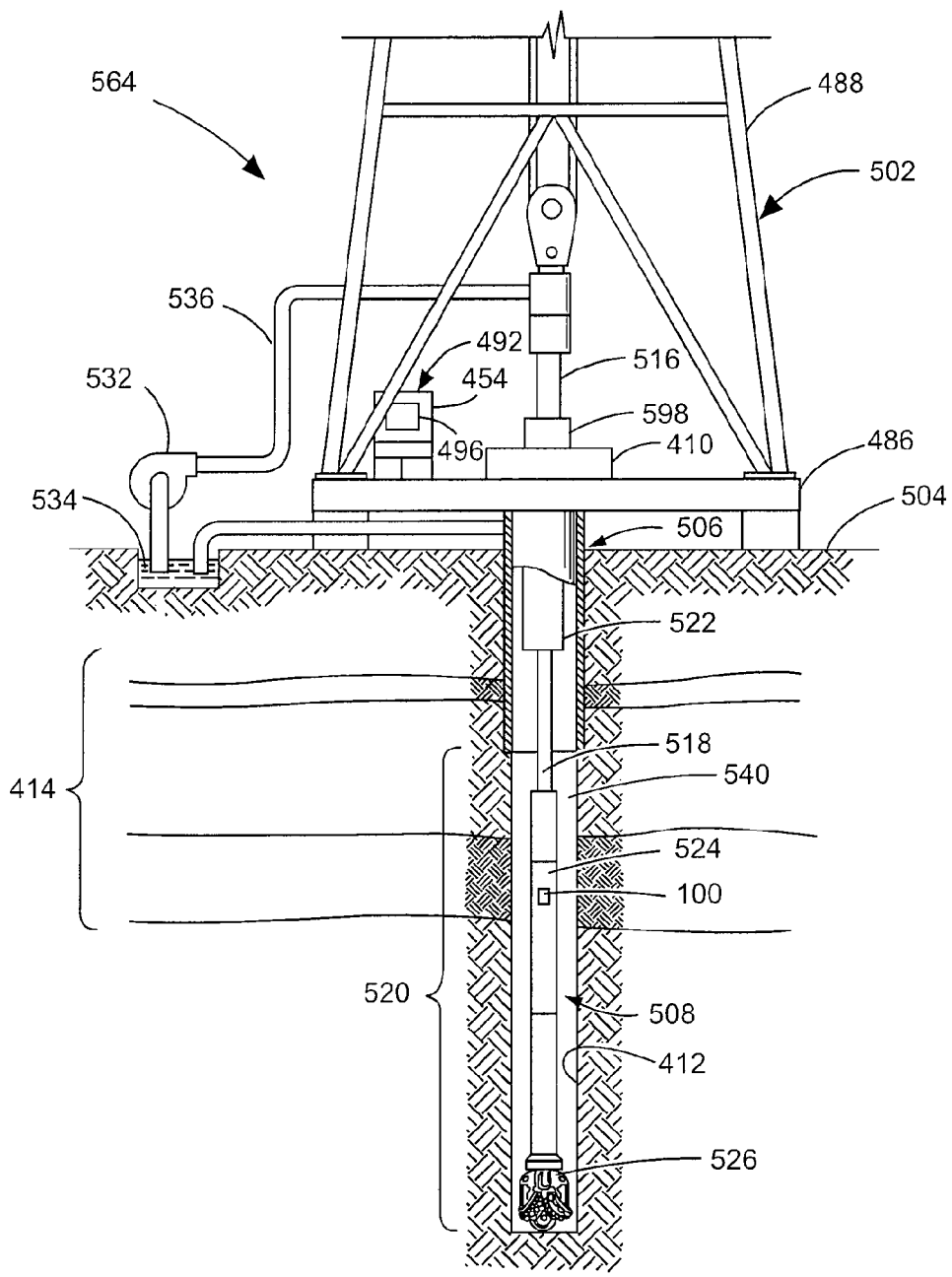
FIG. 5 illustrates a drilling rig system embodiment of the invention.

For example, FIG. 4 illustrates a wireline system 464 embodiment of the invention, and FIG. 5 illustrates a drilling rig system 564 embodiment of the invention. Thus, the systems 102 (see FIG. 1), 464, 564 may comprise portions of a tool body 470 as part of a wireline logging operation, or of a downhole tool 524 as part of a downhole drilling operation. Although it is not shown here, some embodiments can be used in a subsea wireline or drilling environment.

FIG. 4 shows a well during wireline logging operations. A drilling platform 486 is equipped with a derrick 488 that supports a hoist 490.

The drilling of oil and gas wells is commonly carried out using a string of drill pipes connected together so as to form a drilling string that is lowered through a rotary table 410 into a wellbore or borehole 412. Here it is assumed that the drill string has been temporarily removed from the borehole 412 to allow a wireline logging tool body 470, such as a probe or sonde, to be lowered by wireline or logging cable 474 into the borehole 412. Typically, the tool body 470 is lowered to the bottom of the region of interest and subsequently pulled upward at a substantially constant speed.

During the upward trip, at a series of depths the tool movement can be paused and the tool set to pump fluids into the instruments (e.g., via the transport mechanism 106 shown in FIG. 1) included in the tool body 470. Various instruments (e.g., sensors 108 shown in FIGS. 1-2) may be used to perform measurements on the subsurface geological formations 414 adjacent the borehole 412 (and the tool body 470). The measurement data can stored and/or processed downhole (e.g., via subsurface processor(s) 130, logic 140, and memory 146) or communicated to a surface logging facility 492 for storage, processing, and analysis. The logging facility 492 may be provided with electronic equipment for various types of signal processing, which may be implemented by any one or more of the components of the apparatus 100 in FIG. 1. Similar formation evaluation data may be gathered and analyzed during drilling operations (e.g., during logging while drilling (LWD) operations, and by extension, sampling while drilling).

In some embodiments, the tool body 470 comprises a formation testing tool for obtaining and analyzing a fluid sample from a subterranean formation through a wellbore. The formation testing tool is suspended in the wellbore by a wireline cable 474 that connects the tool to a surface control unit (e.g., comprising a workstation 156 in FIG. 1 or 454 in FIGS. 4-5). The formation testing tool may be deployed in the wellbore on coiled tubing, jointed drill pipe, hard-wired drill pipe, or via any other suitable deployment technique.

Turning now to FIG. 5, it can be seen how a system 564 may also form a portion of a drilling rig 502 located at the surface 504 of a well 506. The drilling rig 502 may provide support for a drill string 508. The drill string 508 may operate to penetrate a rotary table 410 for drilling a borehole 412 through subsurface formations 414. The drill string 508 may include a kelly 516, drill pipe 518, and a bottom hole assembly 520, perhaps located at the lower portion of the drill pipe 518.

The bottom hole assembly 520 may include drill collars 522, a downhole tool 524, and a drill bit 526. The drill bit 526 may operate to create a borehole 412 by penetrating the surface 504 and subsurface formations 414. The downhole tool 524 may comprise any of a number of different types of tools including MWD (measurement while drilling) tools, LWD tools, and others.

During drilling operations, the drill string 508 (perhaps including the kelly 516, the drill pipe 518, and the bottom hole assembly 520) may be rotated by the rotary table 410. In addition to, or alternatively, the bottom hole assembly 520 may also be rotated by a motor (e.g., a mud motor) that is located downhole. The drill collars 522 may be used to add weight to the drill bit 526. The drill collars 522 may also operate to stiffen the bottom hole assembly 520, allowing the bottom hole assembly 520 to transfer the added weight to the drill bit 526, and in turn, to assist the drill bit 526 in penetrating the surface 504 and subsurface formations 414.

During drilling operations, a mud pump 532 may pump drilling fluid (sometimes known by those of skill in the art as "drilling mud") from a mud pit 534 through a hose 536 into the drill pipe 518 and down to the drill bit 526. The drilling fluid can flow out from the drill bit 526 and be returned to the surface 504 through an annular area 540 between the drill pipe 518 and the sides of the borehole 412. The drilling fluid may then be returned to the mud pit 534, where such fluid is filtered. In some embodiments, the drilling fluid can be used to cool the drill bit 526, as well as to provide lubrication for the drill bit 526 during drilling operations. Additionally, the drilling fluid may be used to remove subsurface formation cuttings created by operating the drill bit 526.

Thus, referring now to FIGS. 1-5, it may be seen that in some embodiments, a system 102, 464, 564 may include a downhole tool 524, and/or a wireline logging tool body 470 to house one or more apparatus 100, similar to or identical to the apparatus 100 described above and illustrated in FIGS. 1-2. Thus, for the purposes of this document, the term "housing" may include any one or more of a downhole tool 104, 524 or a wireline logging tool body 470 (each having an outer wall that can be used to enclose or attach to instrumentation, sensors, fluid sampling devices, pressure measurement devices, seals, seal location mechanisms, processors, and data acquisition systems). The downhole tool 104, 524 may comprise an LWD tool or MWD tool. The tool body 470 may comprise a wireline logging tool, including a probe or sonde, for example, coupled to a logging cable 474. Baseline values, associated with the sensor and one or more fluids, may be stored in a memory down hole for recall, as needed. Thus, a system 102, 464, 564 may comprise a memory 146 to store the baseline information 158 for one or more sensors 108. In some embodiments, the system 102, 464, 564 may comprise a telemetry transmitter 144 to transmit at least some of the sensor measurement information to the processor(s) 130. Many embodiments may thus be realized.

The apparatus 100; systems 102, 464, 564; downhole tool 104; fluid transport mechanism 106; sensors 108; QGS 110; MCS 112; valves 114; fluid paths 116; filter screen assembly 118; FPS 120; DPS 124; processors 130; borehole seals 138; logic 140; transmitter 144; formation 148; data acquisition system 152; fluid 154; workstation 156, 454; fluid exit 162; pistons 264; outlet port 268; flow line 270; rotary table 410; tool body 470; drilling platform 486; derrick 488; hoist 490; logging facility 492; display 496; drilling rig 502; drill string 508; kelly 516; drill pipe 518; bottom hole assembly 520; drill collars 522; downhole tool 524; drill bit 526; mud pump 532; and hose 536 may all be characterized as "modules" herein. Such modules may include hardware circuitry, and/or a processor and/or memory circuits, software program modules and objects, and/or firmware, and combinations thereof, as desired by the architect of the apparatus 100 and systems 102, 464, 564, and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for logging operations, and thus, various embodiments are not to be so limited. The illustrations of apparatus 100 and systems 102, 464, 564 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules. Such apparatus and systems may further be included as subcomponents within a variety of electronic systems, such as televisions, cellular telephones, personal computers, workstations, radios, video players, vehicles, signal processing for geothermal tools and smart transducer interface node telemetry systems, among others. Some embodiments include a number of methods.

Figure 6:
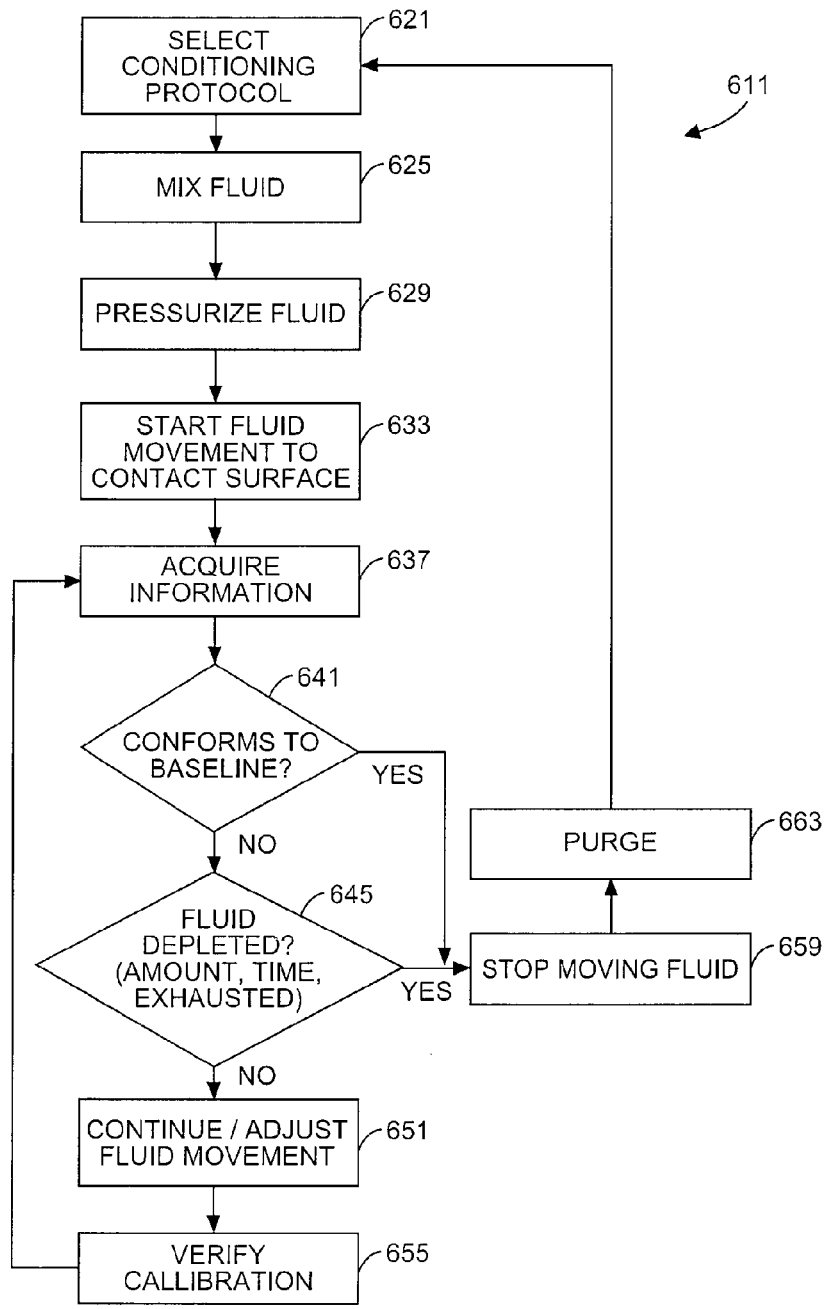
FIG. 6 is a flow chart illustrating several methods according to various embodiments of the invention.

For example, FIG. 6 is a flow chart illustrating several methods 611, according to various embodiments of the invention. For example, in some embodiments of the method 611, fluid is moved to a surface associated with a sensor, where fluid movement is adjusted until sensor readings conform to a baseline reading (according to some desired degree of conformance), or the down hole supply of the fluid is depleted. Conformance is achieved, for example, when the moving fluid operates to clean the sensor.

Thus, a processor-implemented method 611 to execute on one or more processors that perform the method may begin at block 621 with selecting a sensor conditioning protocol. An example protocol might include initiating sensor surface cleaning fluid movement every hour of operation, when temperatures exceed 100 C. Another protocol might include the initiation of fluid movement when the present sensor reading exceeds the highest prior reading by more than 50%, or is less than half of the lowest prior reading. Many other protocols are possible. The fluid may constitute a mixture or a reacted compound. Thus, the method 611 may include at block 625, forming the fluid by mixing a first component from a first fluid container with a second component in one or more second fluid containers.

The fluid may be pressurized to modify its density before being moved to contact the surface associated with the sensor. Thus, the method 611 may continue to block 629 to include pressurizing the fluid using a pump and valves coupled to the flow line to achieve a selected density of the fluid.

The method 611 may continue on to block 633 to include moving the fluid from at least one fluid container into a flow line so as to cause the fluid to contact at least one surface having a condition affecting sensor information provided by a sensor.

The fluid that contacts the surface may comprise a number of components. For example, the fluid may comprise one or more of a salt, an acid, an organic emulsifying agent, an aromatic dye, or an oxidizing agent.

The fluid movement can be arranged to create a desired mixing profile. Thus, the activity at block 633 may comprise moving the fluid to create a fluid interface within the flow line, the fluid interface having a desired mixing profile over distance and/or time.

The fluid can be moved within the flow line in a number of ways, including the use of pumping and/or pressurized pistons. Thus, the activity at block 633 may comprise at least one of pumping the fluid or urging the fluid ahead of a piston in one or more fluid containers, where the piston is driven by pressurized gas.

The method 611 may continue on to block 637 with acquiring information from the sensor. For example, if the sensor is a temperature sensor, this activity would include acquiring temperature readings from the sensor, including an increase or decrease in temperature that would be expected from implementing a given chemical reaction. If the sensor is a density sensor, the activity would include acquiring density readings from the sensor. If the sensor is a resistivity sensor, a test/calibration fluid that moves to a known condition as a function of temperature and pressure, can be used, and so on.

The method 611 may continue on to block 641 to determine whether the sensor information conforms to the baseline information to a selected degree. If so, the method 611 may include halting movement of the fluid at block 659.

Dead volumes or calibration fluid within one or more containers can be purged, as desired, perhaps using formation fluid or pressurized gas. Thus, the method 611 may continue on to block 663 with purging the fluid container of a dead volume or a calibration fluid, using formation fluid or a pressurized gas.

If the sensor information does not conform to the baseline information to a selected degree, as determined at block 641, then the method 611 may continue on to block 645 to determine whether the supply of fluid down hole has been depleted. If so, then the method 611 may continue on to block 659. For the purposes of this document, "depleted" can mean any one of three things: (a) that the supply of a particular fluid down hole has been exhausted, (b) that a preselected amount of fluid has been moved past the surface associated with the sensor, or (c) that the fluid has been moving past the sensor for a preselected amount of time, which has expired. These last two interpretations are useful when the fluid supply is to be conserved by operators of the apparatus and systems described herein—so that a limit on the amount of fluid, or time of fluid movement, is selected before the activity of fluid transport begins.

If the fluid supply is not depleted from the fluid container(s), as determined at block 645, then the method 611 may continue on to block 651, to include adjusting the operation of a fluid transport mechanism based on the sensor information and baseline information, to continue moving the fluid and change the condition of the surface until the fluid is depleted from the at least one fluid container or the sensor information conforms to the baseline information to a selected degree.

The activity of moving the fluid and adjusting fluid movement may be implemented between one or more pumpout stations down hole. Thus, the activity at block 651 may comprise moving the fluid and adjusting the operation of the fluid transport mechanism between multiple pairs of pumpout stations in a borehole.

Movement of the fluid may continue, and be repeated, until sensor calibration is verified. Thus, the method 611 may continue on to block 655, to include verifying calibration of the sensor after adjusting fluid movement, and repeating the fluid movement, and adjusting the fluid movement (e.g., speeding up, slowing down, or reversing direction), if the calibration is not verifiable.

It should be noted that the methods described herein do not have to be executed in the order described, or in any particular order. Moreover, various activities described with respect to the methods identified herein can be executed in iterative, serial, or parallel fashion. Information, including parameters, commands, operands, and other data, can be sent and received in the form of one or more carrier waves.

The apparatus 100 and systems 102, 464, 564 may be implemented in a machine-accessible and readable medium that is operational over one or more networks. The networks may be wired, wireless, or a combination of wired and wireless. The apparatus 100 and systems 102, 464, 564 can be used to implement, among other things, the processing associated with the methods 611 of FIG. 6. Modules may comprise hardware, software, and firmware, or any combination of these. Thus, additional embodiments may be realized.

Figure 7:
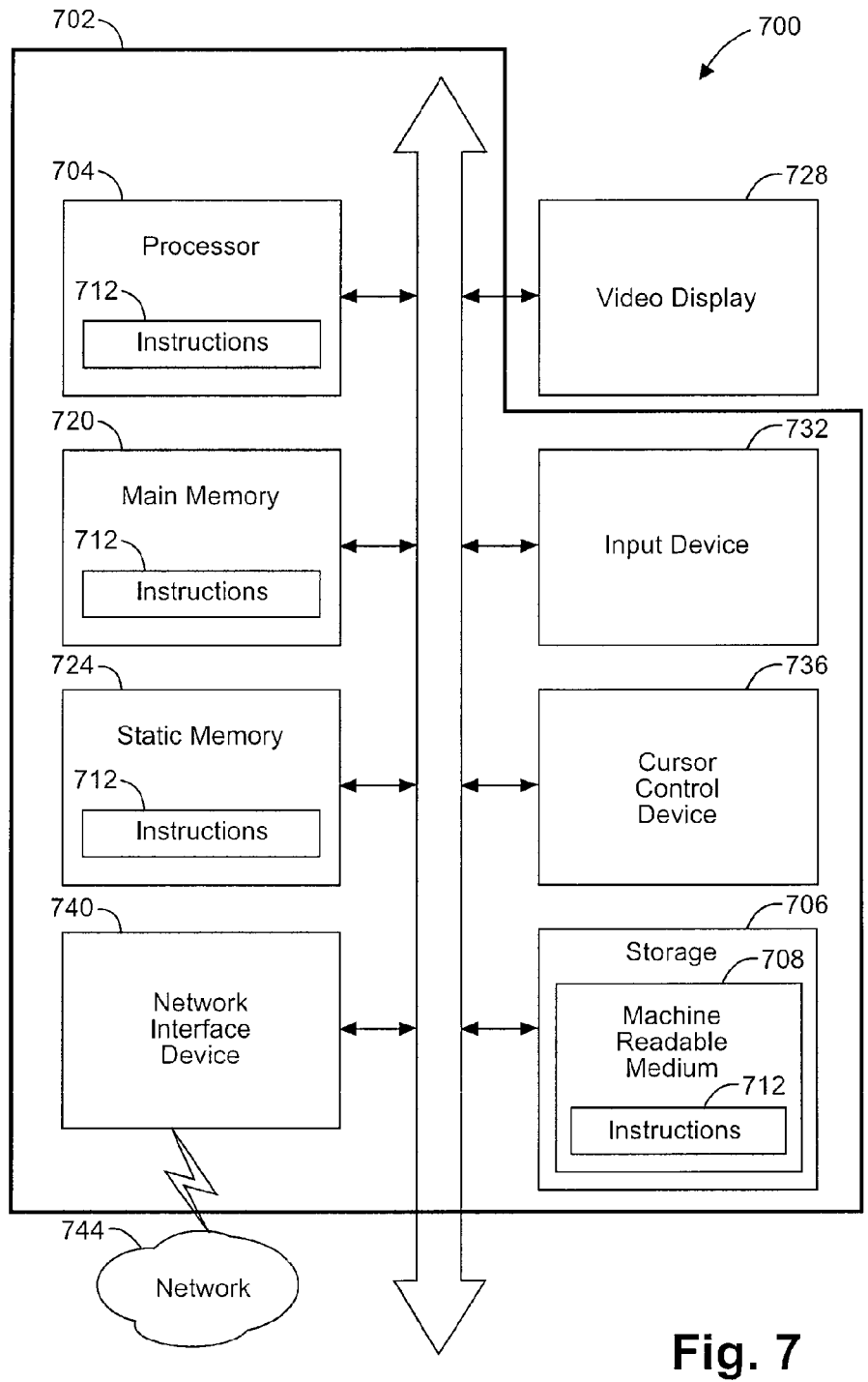
FIG. 7 is a block diagram of an article of manufacture, including a specific machine, according to various embodiments of the invention.

For example, FIG. 7 is a block diagram of an article 700 of manufacture, including a specific machine 702, according to various embodiments of the invention. Upon reading and comprehending the content of this disclosure, one of ordinary skill in the art will understand the manner in which a software program can be launched from a computer-readable medium in a computer-based system to execute the functions defined in the software program.

One of ordinary skill in the art will further understand the various programming languages that may be employed to create one or more software programs designed to implement and perform the methods disclosed herein. The programs may be structured in an object-orientated format using an object-oriented language such as Java or C++. The programs can also be structured in a procedure-oriented format using a procedural language, such as assembly or C. The software components may communicate using any of a number of mechanisms well known to those of ordinary skill in the art, such as application program interfaces or interprocess communication techniques, including remote procedure calls. The teachings of various embodiments are not limited to any particular programming language or environment. Thus, other embodiments may be realized.

For example, an article 700 of manufacture, such as a computer, a memory system, a magnetic or optical disk, some other storage device, and/or any type of electronic device or system may include one or more processors 704 coupled to a machine-readable medium 708 such as a memory (e.g., removable storage media, as well as any memory including an electrical, optical, or electromagnetic conductor) having instructions 712 stored thereon (e.g., computer program instructions), which when executed by the one or more processors 704 result in the machine 702 performing any of the actions described with respect to the methods above.

The machine 702 may take the form of a specific computer system having a processor 704 coupled to a number of components directly, and/or using a bus 716. Thus, the machine 702 may be incorporated into the apparatus 100 or systems 102, 464, 564 shown in FIGS. 1-5, perhaps as part of the processor 130, or the workstation 454.

Turning now to FIG. 7, it can be seen that the components of the machine 702 may include main memory 720, static or non-volatile memory 724, and mass storage 706. Other components coupled to the processor 704 may include an input device 732, such as a keyboard, or a cursor control device 736, such as a mouse. An output device 728, such as a video display, may be located apart from the machine 702 (as shown), or made as an integral part of the machine 702.

A network interface device 740 to couple the processor 704 and other components to a network 744 may also be coupled to the bus 716. The instructions 712 may be transmitted or received over the network 744 via the network interface device 740 utilizing any one of a number of well-known transfer protocols (e.g., HyperText Transfer Protocol). Any of these elements coupled to the bus 716 may be absent, present singly, or present in plural numbers, depending on the specific embodiment to be realized.

The processor 704, the memories 720, 724, and the storage device 706 may each include instructions 712 which, when executed, cause the machine 702 to perform any one or more of the methods described herein. In some embodiments, the machine 702 operates as a standalone device or may be connected (e.g., networked) to other machines. In a networked environment, the machine 702 may operate in the capacity of a server or a client machine in server-client network environment, or as a peer machine in a peer-to-peer (or distributed) network environment.

The machine 702 may comprise a personal computer (PC), a tablet PC, a set-top box (STB), a PDA, a cellular telephone, a web appliance, a network router, switch or bridge, server, client, or any specific machine capable of executing a set of instructions (sequential or otherwise) that direct actions to be taken by that machine to implement the methods and functions described herein. Further, while only a single machine 702 is illustrated, the term "machine" shall also be taken to include any collection of machines that individually or jointly execute a set (or multiple sets) of instructions to perform any one or more of the methodologies discussed herein.

While the machine-readable medium 708 is shown as a single medium, the term "machine-readable medium" should be taken to include a single medium or multiple media (e.g., a centralized or distributed database, and/or associated caches and servers, and or a variety of storage media, such as the registers of the processor 704, memories 720, 724, and the storage device 706 that store the one or more sets of instructions 712. The term "machine-readable medium" shall also be taken to include any medium that is capable of storing, encoding or carrying a set of instructions for execution by the machine and that cause the machine 702 to perform any one or more of the methodologies of the present invention, or that is capable of storing, encoding or carrying data structures utilized by or associated with such a set of instructions. The terms "machine-readable medium" or "computer-readable medium" shall accordingly be taken to include tangible media, such as solid-state memories and optical and magnetic media.

Various embodiments may be implemented as a standalone application (e.g., without any network capabilities), a client-server application or a peer-to-peer (or distributed) application. Embodiments may also, for example, be deployed by Software-as-a-Service (SaaS), an Application Service Provider (ASP), or utility computing providers, in addition to being sold or licensed via traditional channels.

Using the apparatus, systems, and methods disclosed herein may afford formation evaluation clients the opportunity to more intelligently choose between repeating measurements and moving the tool. Various embodiments may enable verifying the quality of sensor measurement data in situ. The accuracy of acquired information, and client satisfaction, may be increased as a result.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

The invention claimed is:

1. An apparatus, comprising:
at least one fluid container coupled to a flow line;
a sensor;
at least one surface having a condition affecting sensor information provided by the sensor;
a fluid transport mechanism to move fluid from the at least one fluid container into the flow line, to cause the fluid to contact the at least one surface; and
a processor arranged with a feedback mechanism to adjust operation of the fluid transport mechanism based on the sensor information and baseline information, to move the fluid and change the condition of the at least one surface to recondition the at least one surface until the fluid is depleted or the sensor information conforms to the baseline information to a selected degree.

2. The apparatus of claim 1, wherein the sensor comprises one of an optical sensor, a densitometer, or a resistivity sensor.

3. The apparatus of claim 1, wherein the surface comprises one of a surface on the sensor or an optical window to direct radiated energy to the sensor.

4. The apparatus of claim 1, wherein the fluid transport mechanism is reversible to selectably move the fluid in a first direction across the surface and in a second direction across the surface that is opposite to the first direction.

5. The apparatus of claim 1, further comprising:
multiple ones of the at least one fluid container and the valve to permit mixing multiple fluids, including the fluid, with each other under control of the processor, wherein the fluid transport mechanism can be configured to move a mixture of selected ones of the multiple fluids to the sensor.

6. The apparatus of claim 1, wherein the fluid container comprises:
a first outlet port coupled to the flow line, and a second outlet port coupled to another sensor, the other sensor to provide fluid property information to the processor.

7. The apparatus of claim 1, wherein the fluid transport mechanism comprises:
at least one of a pump, an accumulator, or a valve.

8. The apparatus of claim 1, wherein the fluid container comprises a flow-through fluid container with at least one inlet and at least one outlet.

9. The apparatus of claim 1, wherein the fluid from the at least one fluid container is a cleaning fluid to clean the at least one surface.

10. A system, comprising:
a down hole tool housing; and
an apparatus attached to the housing, the apparatus comprising:
at least one fluid container coupled to a flow line with a valve;
a sensor;
at least one surface having a condition affecting sensor information provided by the sensor;
a fluid transport mechanism to move fluid from the at least one fluid container into the flow line, to cause the fluid to contact the at least one surface; and
a processor arranged with a feedback mechanism to adjust operation of the valve and/or the fluid transport mechanism based on the sensor information and baseline information, to move the fluid and change the condition of the at least one surface to recondition the at least one surface until the fluid is depleted or the sensor information conforms to the baseline information to a selected degree.

11. The system of claim 10, wherein the down hole tool housing comprises one of a wireline tool or a measurement while drilling tool.

12. The system of claim 10, further comprising:
a memory to store the baseline information for the sensor and for at least one other sensor.

13. A processor-implemented method to execute on one or more processors that perform the method, comprising:
moving fluid from at least one fluid container into a flow line so as to cause the fluid to contact at least one surface having a condition affecting sensor information provided by a sensor; and
adjusting using a feedback mechanism, operation of a fluid transport mechanism based on the sensor information and baseline information, to continue moving the fluid and change the condition of the at least one surface to recondition the at least one surface until the fluid is depleted from the at least one fluid container or the sensor information conforms to the baseline information to a selected degree.

14. The method of claim 13, wherein the fluid comprises at least one of a salt, an acid, an organic emulsifying agent, an aromatic dye, or an oxidizing agent.

15. The method of claim 13, further comprising:
prior to moving the fluid, forming the fluid by mixing a first component from another fluid container with a second component in the at least one fluid container.

16. The method of claim 13, further comprising:
prior to moving the fluid, pressurizing the fluid using a pump and valves coupled to the flow line to achieve a selected density of the fluid.

17. The method of claim 13, wherein the moving further comprises:
moving the fluid to create a fluid interface within the flow line, the fluid interface having a desired mixing profile over at least one of distance or time.

18. The method of claim 13, wherein the moving further comprises:
at least one of pumping the fluid or urging the fluid ahead of a piston in the fluid container, the piston driven by pressurized gas.

19. The method of claim 13, further comprising:
purging the fluid container of a dead volume or a calibration fluid using formation fluid or a pressurized gas.

20. The method of claim 13, further comprising:
moving the fluid and adjusting the operation of the fluid transport mechanism between multiple pairs of pumpout stations in a borehole.

21. The method of claim 13, further comprising:
verifying calibration of the sensor after the adjusting, and repeating the moving and the adjusting if the calibration is not verifiable.

* * * * *